United States Patent
Resconi

(10) Patent No.: US 6,774,253 B1
(45) Date of Patent: Aug. 10, 2004

(54) PROCESS FOR THE PREPARATION OF TITANIUM COMPLEXES

(75) Inventor: Luigi Resconi, Ferrara (IT)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 09/762,125

(22) PCT Filed: Jan. 31, 2000

(86) PCT No.: PCT/EP00/00747

§ 371 (c)(1),
(2), (4) Date: Feb. 2, 2001

(87) PCT Pub. No.: WO00/75151

PCT Pub. Date: Dec. 14, 2000

(30) Foreign Application Priority Data

Jun. 4, 1999 (EP) ............................................. 99201769

(51) Int. Cl.$^7$ ............................ C07F 17/00; B01J 31/00
(52) U.S. Cl. ............................... 556/11; 556/7; 556/12; 556/20; 556/22; 556/28; 556/53; 556/56; 556/58; 526/160; 526/943; 503/103; 503/117
(58) Field of Search ............................... 556/11, 12, 20, 556/22, 28, 53, 56, 58, 7; 502/103, 117; 526/160, 943

(56) References Cited

U.S. PATENT DOCUMENTS

| | | | | |
|---|---|---|---|---|
| 5,504,223 A | * | 4/1996 | Rosen et al. | 556/7 |
| 5,512,693 A | | 4/1996 | Rosen et al. | 556/7 |
| 5,631,391 A | * | 5/1997 | Canich | 556/11 |
| 5,866,704 A | * | 2/1999 | Nickias et al. | 556/11 |

FOREIGN PATENT DOCUMENTS

| | | | | |
|---|---|---|---|---|
| EP | 0416815 | 3/1991 | ........... | C08F/10/00 |
| EP | 0420436 | 4/1991 | ........... | C07F/7/00 |
| EP | 0575875 | 12/1993 | ........... | C08F/4/642 |
| EP | 0643066 | 3/1995 | ........... | C07F/17/00 |
| EP | 0671404 | 9/1995 | ........... | C07F/17/00 |
| WO | 9104257 | 4/1991 | ........... | C07F/7/00 |
| WO | 9519984 | 7/1995 | ........... | C07F/19/00 |
| WO | 9602580 | 2/1996 | ........... | C08F/4/642 |
| WO | 9608498 | 3/1996 | ........... | C07F/7/00 |
| WO | 9710248 | 3/1997 | ........... | C07F/17/00 |
| WO | 9806727 | 2/1998 | ........... | C07F/17/00 |
| WO | 9921899 | 5/1999 | ........... | C08F/10/02 |
| WO | 9936427 | 7/1999 | ........... | C07F/17/00 |
| WO | 0121674 | 3/2001 | ........... | C08F/10/00 |

OTHER PUBLICATIONS

A. McKnight et al., Organometallics, 16: 2879–2885 (1997).
F. Amor et al., Journal of Organometallic Chemistry, 520: 245–248 (1996).
You–Xian Chen et al., Organometallics, 16: 3649–3657 (1997).
W. Herrmann et al., Journal of Organometallic Chemistry, 482: 169–181 (1994).

* cited by examiner

*Primary Examiner*—Porfirio Nazario-Gonzalez

(57) ABSTRACT

A new process is disclosed, particularly simple, convenient and practical, for the direct synthesis of titanium complexes of the formula (I): $(D)(ZR^1_m)_n(A)TiL_pX_q$, wherein $(ZR^1_m)_n$ is a divalent group bridging D and A; D is a delocalized π-bonded moiety, which is bound in an $\eta^5$ bonding mode to Ti, and is preferably a Cp moiety; A is —O—, —S—, —N($R^2$)— or —P($R^2$)—, wherein $R^2$ is hydrogen, alkyl, cycloalayl, aryl, alkylaryl or arylalkl; L are monoanionic sigma ligands selected from alkyl, cycloalkyl, aryl, alkylaryl and arylalkyl groups; m is 1 or 2; n is 1–3; p is 1 or 2, q is 0 or 1 and p+q=2; said process comprises reacting a ligand of formula $(H—D)(ZR^1_m)_n(A—H)$ with about 1 molar equivalent of $TiX_4$ in the presence of about (2+p) molar equivalent of $L_jB$ or LMgX wherein X is halogen or —OR', B is an alkaline or alkaline-earth metal, and j is 1 or 2.

15 Claims, No Drawings

PROCESS FOR THE PREPARATION OF TITANIUM COMPLEXES

This application is the U.S. national phase of International Application PCT/EP00/00747, filed Jan. 31, 2000.

FIELD OF THE INVENTION

The present invention relates to a new process, particularly simple, convenient and practical, for the preparation of complexes of titanium, preferably monocyclopentadienyl titanium dihydrocarbyl complexes; more specifically, it relates to a process for the direct synthesis of complexes wherein the titanium atom is linked to two sigma ligands selected from the group consisting of linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing Si or Ge atoms.

These complexes are useful as catalyst components in the polymerization of olefins, in association with suitable activating cocatalysts.

PRIOR ART DISCLOSURE

Homogeneous catalytic systems based on constrained geometry catalysts in association with useful cocatalysts are well known in the state of the art and are widely used in the polymerization reaction of olefins, as described for instance in EP-A-416,815, EP-A-420,436, EP-A-671,404, EP-A-643,066 and WO 91/04257.

These homogeneous catalytic systems are based on monocyclopentadienyl metal dihalide coordination complexes, wherein the sigma ligands of the central metal atom are halogen, and usually chlorine.

In known prior art processes, the synthesis of the metal dihalide complexes is often troublesome and much lower than quantitative. Said complexes may be produced by contacting the metal reactant (usually $MX_4$) and a group I metal salt (usually the dilithium salt) or a Grignard salt of the cyclopentadienyl compound; while this reaction may be favorably carried out to produce zirconium dihalide complexes, it shows only very poor yields in the production of titanium dihalide complexes, due to the reduction of Ti(IV) to Ti(III).

For instance, M. Waymouth et al. (*Organometallics* 16:2879–2885, 1997) prepared indenyl-amido titanium dichloride complexes by treating the dilithium salt of (tert-butylamido)(dimethyl)(indenyl)silane (obtained by reacting the ligand with 2BuLi) with $TiCl_4(THF)_2$; the yields for this synthesis were quite low (<20%).

Besides the very low final yields, said reactions have the disadvantage of requiring very low temperatures (−78° C.). In fact, the dianion of the monocyclopentadienyl ligand compound requires a multi-step, laborious recovery and purification procedure, before being reacted with an halogenating agent.

Another disadvantage resides in the fact that, since the reaction has to be carried out in aprotic polar solvents, in order to facilitate the handling of the metal tetrahalide reactant which is air and moisture sensitive, prior to the reaction step the transition metal tetrahalide compound is typically converted to its ether-adduct in a separate step with THF or diethyl ether. This adduct formation step in itself proceeds with difficulty, requiring low to very low temperatures, and an inert atmosphere. The adduct is usually recovered before it is reacted with the dianionic derivative of the ligand. The yield of the adduct formation steps is less than quantitative.

Furthermore, the reaction mixture of the transition metal tetrahalide compound and the dianion of the bridged cyclopentadienyl ligand compound requires a multi-step, laborious recovery and purification procedure. Typically, after the reaction step, the solvent is removed, the product re-dissolved by adding dichloromethane or toluene or a mixture thereof, the metal halide byproduct (typically lithium chloride) removed by filtration of the mixture, the solvent removed at least partially, followed by re-dissolving the solid product and crystallizing the product, optionally followed by one or more further recrystallization procedures.

In a preferred process known in the state of the art, the dianionic salt of the monocyclopentadienyl ligand is reacted with a metal compound wherein the metal is in a lower oxidation state than in the desired final complex, for instance Ti(III) compounds; thereafter, the resulting complex has to be contacted with an oxidizing agent (such as AgCl or $PbCl_2$), in order to raise the oxidation state of the metal to form the desired titanium (IV) dihalide complex.

Apart from requiring an extra reaction step (i.e. the oxidation step), the intermediate monohalide coordination complex of Ti(III) is thermally unstable; therefore, reaction yields are usually unsatisfactory.

For instance, in *Organometallics* 16:2879–2885, 1997 is described the preparation of a bridged mono(substituted cyclopentadienyl) titanium dichloride complex by treating the THF-adduct of $TiCl_3$ with the dimagnesium salt of [(R-amide)dimethylsilyl](tert-butyl)cyclopentadienide (obtained by deprotonation of the ligand with iPrMgCl), followed by $PbCl_2$ oxidation; the yields were only of 52% in case of R=tBu and 16% in case of R=CHMePh. Moreover, in the case of indenyl-amido titanium complexes, reaction of the indenyl dimagnesium dichloride salts with $TiCl_3(THF)_3$ followed by $PbCl_2$ oxidation was completely unsuccessful.

The corresponding dihydrocarbon derivatives, particularly dimethyl ones, have been developed and are widely used as catalyst components for olefin polymerization reactions, in association with suitable cocatalysts, such as alumoxanes and borate salts, e.g.

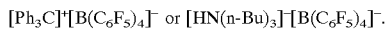

$[Ph_3C]^+[B(C_6F_5)_4]^-$ or $[HN(n\text{-}Bu)_3]^+[B(C_6F_5)_4]^-$.

When the sigma ligands of the central metal atom are alkyl or aryl groups, the above metal complexes may not be expediently synthesized by the existing methodology; in fact, prior art processes imply always the synthesis of the metal complex dihalide, that is subsequently hydrocarbylated by ligand exchange with an appropriate hydrocarbylating agent to the target product, thus leading to unsatisfactory total yields and requiring at least the following two process steps:

(1) preparing the halide metal coordination complex, usually the dichloride, by reacting a suitable ligand with $MX_4$, wherein X is halogen (usually $TiCl_4(THF)_2$ or $ZrCl_4$); or alternatively preparing the halide metal coordination complex by reacting a suitable ligand with $MX_3$ (usually $TiCl_3(THF)_3$) and thereafter contacting the product with an oxidizing agent (usually AgCl or $PbCl_2$);

(2) converting the dihalide complex obtained in step (1) into the corresponding dialkyl complex, by substitution of the halogens linked to the metal atom with the desired alkyl or aryl groups, by means of an alkylating agent such as alkyllithium, dialkylmagnesium or the corresponding Grignard reagent.

As already evidenced above, process step (1), leading to the metal monohalide complex, is often troublesome (requiring very low reaction temperatures) and not quantitative; in particular, very poor yields are obtained when $TiCl_4$ or its adducts are used as reactants, due to the abundant reduction of the metal. On the opposite, in case that Ti(III) derivatives are used as the reactants, more acceptable yields are obtained, but the resulting dihalide complex has to be contacted with an oxidizing agent, in order to raise the oxidation state of the metal to form the desired dihalide complex. Therefore, these preparation processes inherently have the disadvantages associated with the preparations of the metal dihalide complexes.

Finally, in order to achieve the desired dialkyl metal complex, the metal dichloride complex has to be treated with an alkylating agent, such as MeLi (step (2)); therefore, a further reaction step is required thus lowering notably the total reaction yields and rendering the whole process more laborious and time consuming.

According to the literature procedures (Jun Okuda et al., *Journal of Organometallic Chemistry*, 520:245–248, 1996), dimethylsilandiyl(tert-butylamido)(indenyl) titanium dimethyl can be obtained at best in two reaction steps, in an unsatisfactory total yield. More specifically, in the cited reference, Okuda obtained the above Ti(IV) dichloride complex by the reaction of the dilithium derivative Li$_2$[Ind-SiMe$_2$-NCMe$_3$] (obtained in a yield of 90% by reacting the ligand and BuLi, at low temperature) with a suspension of TiCl$_3$(THF)$_3$ in THF, followed by oxidation using PbCl$_2$ of the obtained titanium (III), in a yield of 94%. The Ti(IV) dichloride complex was then alkylated at −78° C. by reacting the dihalide metal complex with methylmagnesium chloride, thus obtaining the dimethyl complex Ti[Ind-SiMe$_2$-NCMe$_3$]Me$_2$ in 49% yield; therefore, starting from the ligand, the resulting total yield is not satisfactory (90·94·49/10,000=41.5%).

J. Marks et al. (*Organometallics*, 16:3649–3657, 1997) obtained the synthesis of dimethylsilandiyl(tert-butylamido)(η$^5$-tetramethyl-cyclopentadienyl) titanium dimethyl in an unsatisfactory total yield of 31.7%, with the following steps: 1) reaction the ligand of (tert-butylamido)(dimethyl)(η$^5$-tetramethyl-cyclopentadienyl)silane with 2BuLi in Et$_2$O at −78° C., to give the ligand dilithium salt in 90% yield; 2) reacting the obtained dilithium salt with the appropriate metal halide (TiCl$_3$(THF)$_3$) at very low temperature (−78° C), followed by oxidation with PbCl$_2$ or AgCl, with a yield of 63%; 3) final alkylation of the obtained metal dichloride with MeLi, at very low temperature (−78° C.), with a yield of 56%. Therefore, the above synthesis provides the desired titanium dialkyl complex in an overall yield lower than 32%, with three cooling cycles.

In regard to alternative synthetic strategies for the production of titanium monocyclopentadienyl-amido complexes, the Ti(NR$_2$)$_4$ precursor amine elimination approach has provided in general a more efficient preparation than conventional salt elimination synthetic routes (see W. A. Herrmann et al., *Journal of Organometallic Chemistry*, 482:169–181, 1994).

However, in the above cited reference (*Organometallics*, 16:3649–3657, 1997), this route is reported to be unsuitable for titanium diamido complexes (ligand)Ti(NMe$_2$)$_2$ and leads instead to a myriad of undesired products (while for Zr complexes, only a single product is afforded).

Furthermore, although the amine elimination route provides an efficient preparation of Cp-unsubstituted Me$_2$Si(C$_5$H$_4$)(tBuN)M(NMe$_2$)$_2$ (M=Ti or Zr) analogues, the amido complexes cannot be protonically converted to the corresponding dichloride derivatives without the formation of dimethylamine adducts.

For subsequent catalysis, it is critical that the amido complexes be converted to dichloride or ideally to dialkyl polymerization catalyst precursors, because amido-derived catalysts are significantly less active than chloride or alkyl-derived catalysts.

An alternative synthetic route is reported in the international patent application WO 95/19984, which describes a process for preparing bridged mono- and bis (cyclopentadienyl) metal dihydrocarbyloxy coordination complexes by contacting, in the presence of an aprotic organic diluent, a metal compound of formula M(OR)$_4$ with the dianionic salt of the corresponding ligand; by treatment of said metal dihydrocarbyloxy coordination complexes with a hydrocarbylation agent or an halogenation agent, the corresponding metal dihydrocarbyl or dihalide coordination complexes may be obtained.

Also in this case, in order to achieve the desired dialkyl metal complex, it is necessary to pass through the metal dihydrocarbyloxy derivative; although this process avoids the disadvantages associated with the preparations of the metal dihalide complexes, it requires a further reaction step, thus lowering the total reaction yields and rendering the whole process more laborious and time consuming.

Therefore, the prior art processes for producing constrained geometry catalysts, and in general metal complexes having hydrocarbon sigma ligands bonded to the central metal atom, are inadequate for a commercially viable and practical production of said derivatives, for use as catalyst components in olefin polymerization; it is felt the need for a simpler and more convenient and practical method to produce the above metal derivatives in satisfactory yields. The international patent application WO 99/36427 (appl. no. PCT/EP 99/00188), in the name of the same Applicant, describes a process for the preparation of metallocene compounds of formula (I):

(Cp)(ZR$^1_m$)$_n$(A)$_r$ML$_p$L'$_q$  (I)

wherein (ZR$^1_m$)$_n$ is a divalent group bridging Cp and A, Z being C, Si, Ge, N or P, and the R$^1$ groups being hydrogen or hydrocarbon groups;

Cp is a cyclopentadienyl group;

A is a cyclopentadienyl group or may be —O—, —S— or —N(R$^2$)—, wherein R$^2$ is hydrogen or an hydrocarbon group;

M is a transition metal of groups 3–6 or of the lanthanide or actinide groups; the substituents L are monoanionic hydrocarbon sigma ligands;

the substituents L' are halogens or —OR, wherein R is hydrogen or an hydrocarbon group;

m is 1 or 2; n is 0–4; r is 0 or 1; p is 1–3; and q is 0–2.

The process comprises reacting a ligand of formula (Y-Cp)(ZR$^1_m$)$_n$(A—Y)$_r$ with at least (1+r+p) molar equivalents of a compound of formula L$_j$B or LMgL', wherein Cp, A, Z, R$^1$, m, n, p, r, L and L' have the meaning reported above; the groups Y, the same or different from each other, are suitable leaving groups; B is an alkaline or alkaline-earth metal; and j is 1 or 2, j being equal to 1 when B is an alkaline metal, and j being equal to 2 when B is an alkaline-earth metal; and reacting the product obtained from step (1) with at least 1 molar equivalent of a compound of formula ML'$_s$, wherein M and L' have the meaning reported above; s is an integer corresponding to the oxidation state of the metal and ranges from 3 to 6.

The described process is used in the preparation of metallocenes of Ti, Zr or Hf, preferably of bis-cyclopentadienyl metallocenes of Zr. All the examples refer to the preparation of dialkyl derivatives of Zr.

SUMMARY OF THE INVENTION

The Applicant has now unexpectedly found a new process for the preparation of titanium complexes having hydrocarbon sigma ligands bonded to the central metal atom; more specifically, it is an object of the present invention a direct one-pot synthesis of titanium complexes having formula (I):

(D)(ZR$^1_m$)$_n$(A)TiL$_p$X$_q$  (I)

wherein:

(ZR$^1_m$)$_n$ is a divalent group bridging D and A, Z being C, Si, Ge, N, P or B, and the R$^1$ groups, equal or different from each other, being hydrogen or linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl or C$_7$–C$_{20}$ arylalkyl groups; or two R$^1$ may form together a ring; m is 1 or 2; n is an integer ranging from 1 to 3;

D is a delocalized π-bonded moiety, which is bound in a η$^5$ bonding mode to Ti, and preferably is a substituted or unsubstituted cyclopentadienyl moiety (herein referred to as Cp);

A is a divalent anionic group selected from —O—, —S—, —N(R$^2$)— or —P(R$^2$)—, wherein R$^2$ is hydrogen, a linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl or C$_7$–C$_{20}$ arylalkyl, optionally containing —OR', —SR', —NR'$_2$, or —PR'$_2$, groups, wherein R' is a C$_1$–C$_{10}$ alkyl group;

Ti is titanium;

the substituents L, same or different from each other, are monoanionic sigma ligands selected from the group consisting of linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl and C$_7$–C$_{20}$ arylalkyl groups, optionally containing one or more Si or Ge atoms; preferably, the substituents L are the same;

X is halogen or —OR', wherein R' is a C$_1$–C$_{10}$ alkyl group;

p is 1 or 2, preferably 2; q is 0 or 1, and p+q=2 said process being characterized by comprising the following steps:

(1) reacting a ligand of formula (H—D)(ZR$^1_m$)$_n$(A—H) with about (2+p) molar equivalents of a compound of formula L$_j$B or LMgX, wherein D, A, Z, R$^1$, m, n, p, L and X have the meaning reported above; B is an alkaline or alkaline-earth metal; j is 1 or 2, j being equal to 1 when B is an alkaline metal, and j being equal to 2 when B is an alkaline-earth metal; and (2) reacting the product obtained from step (1) with about 1 molar equivalent of a compound of formula TiX$_4$, wherein X has the meaning reported above.

DETAILED DESCRIPTION OF THE INVENTION

The process of the invention allows to obtain titanium complexes wherein the metal atom bears one or two sigma-bonded hydrocarbon substituents, in a simple, rapid and economic way, leading to the desired products with a one-step process starting from the suitable ligands; furthermore, said process leads to final yields much higher than the ones obtainable with the procedures known in the state of the art, therefore allowing a convenient industrial exploitation of the above metallocene compounds as catalyst components in the polymerization of olefins. The very good yields obtainable with the process according to the present invention are totally unexpected in the light of the results obtained in the prior art literature by contacting a titanium reactant (such as TiX$_4$) and the dilithium salt of the cyclopentadienyl ligand; as already evidenced above, in that case, only poor yields were obtained in the production of titanium dihalide complexes, due to the partial reduction of Ti(IV) to Ti(III).

On the opposite, in the process of the invention the reduction of Ti(IV) is unexpectedly negligible, thus leading to the desired complex in high yields.

In the titanium complexes of formula (I), the divalent bridge (ZR$^1_m$)$_n$ is preferably selected from the group consisting of CR$^1_2$, (CR$^1_2$)$_2$, (CR$^1_2$)$_3$, CR$^1$=CR$^1$, SiR$^1_2$, (SiR$^1_2$)$_2$, CR$^1_2$—SiR$^1_2$, GeR$^1_2$, NR$^1$, PR$^1$ and BR$^1$, R$^1$ having the meaning reported above; more preferably, said divalent bridge is Si(CH$_3$)$_2$, SiPh$_2$, CH$_2$, (CH$_2$)$_2$, (CH$_2$)$_3$ or C(CH$_3$)$_2$.

The variable m is 1 or 2; the variable n ranges from 1 to 3 and, when n>1, the atoms Z can be the same or different from each other, such as in divalent bridges —CH$_2$—O—, —CH$_2$—S— and —CH$_2$—Si(CH$_3$)$_2$—.

The integer n ranges from 1 to 3, and it is preferably 1 or 2.

D is a delocalized π-bonded moiety, which is bound in a η$^5$ bonding mode to Ti; by the use of the term "delocalized π-bonded moiety" is meant an unsaturated organic moiety, such as those comprising ethylenic or acetylenic functionality, wherein the π-electrons thereof are donated to the metal to form a bond. Examples include alkene-, alkenyl-, alkyne-, alkynyl-, allyl-, polyene- and polyenyl-moieties, as well as unsaturated cyclic systems.

The D moiety is preferably a substituted or unsubstituted cyclopentadienyl group (herein referred to as Cp), optionally condensed to one or more substituted or unsubstituted, saturated, unsaturated or aromatic rings. More preferably, Cp is selected from the group consisting of cyclopentadienyl, mono-, di-, tri- and tetra-methyl cyclopentadienyl; 3-tbutyl-cyclopentadienyl; 3-adamantyl-cyclopentadienyl; indenyl; 2-methyl-indenyl; 4,7-dimethyl-indenyl; 3-tbutyl-indenyl; 3-isopropyl-indenyl; benzoindenyl; 4,5,6,7-tetrahydroindenyl; fluorenyl; tetrahydrofluorenyl; octahydrofluorenyl; N-methyl- and N-phenyl-5,10-dihydroindeno [1,2-b]indol-10-yl; N-methyl- and N-phenyl-5,6-dihydroindeno[2,1-b]indol-6-yl; azapentalen4-yl; thiapentalen-4-yl; azapentalen-6-yl; thiapentalen-6-yl; mono-, di- and tri-methyl-azapentalen4-yl.

According to an embodiment of the process of the invention, the Cp moiety may be a cyclopentadienyl group bearing an heteroatom substituent (such as an amino or hydrocarbyloxy groups) in the 3 position, such as 3-heteroatom substituted indenyl group, as described in WO 98/06727.

According to another embodiment, D is a cyclic or non-cyclic, non-aromatic, anionic, dienyl ligand group, as described in WO 96/08498; preferably, said dienyl ligand is a derivative of a pentadienyl, cyclohexadienyl, cyclosilahexadienyl, cycloheptadienyl, cyclooctadienyl, partially hydrogenated anthracenyl, partially hydrogenated naphthalenyl group, or a hydrocarbyl, silyl, hydrocarbyloxy or siloxy substituted derivative thereof According to a most preferred embodiment, D is a (2,4-disubstituted pentadien-3-yl), (2,4-disubstituted pentadien-1-yl), (1,5-disubstituted pentadien-3-yl), (6,6-disubstituted-η$^5$-cyclohexadien-3-yl), (6,6-disubstituted-η$^5$-cyclosilahexadien-3-yl), (1,2,3,4,5-η-cyclohexadien-6-yl), (6-substituted-1,2,3,4,5-η-cyclohexadien-6-yl), (1,2,4,5,6, 6-hexasubstituted-η$^5$-cyclohexadien-3-yl), (1,1-disubstituted-η$^5$-hexahydronaphthalen-4-yl), (1,1,2,3-tetrasubstituted-η$^5$-hexahydronaphthalen-4-yl) or (9,9-disubstituted-10,11,12,13,14-η-1,2,3,4,5,6,7,8,9,10-decahydroanthracene-10-yl), said substituents independently in each occurrence being hydrocarbyl, silyl or a mixture thereof of up to 10 non-hydrogen atoms each.

Further D moieties suitable in the titanium complexes of formula (I) are open-pentadienyl groups, wherein the six π electron systems are not constrained to a five membered ring, as described by the same Applicant in WO 97/10248.

The group A is selected from —O—, —S—, —N(R$^2$)— and —P(R$^2$)—, wherein R$^2$ is defined as above; said group A is preferably —N(R$^2$)— or —P(R$^2$)—, i.e. an amido or phosphido group, wherein R$^2$ is preferably a linear or branched C$_1$–C$_{10}$ alkyl or a C$_7$–C$_{15}$ arylalkyl; even more preferably, R$^2$ is selected from the group consisting of methyl, ethyl, propyl, butyl, pentyl, hexyl and isomers of these alkyl radicals, norbornyl, benzyl and phenyl.

The group R$^2$ may optionally contain —OR', SR', —NR'$_2$ or —PR'$_2$ groups, wherein R' is a C$_1$–C$_{10}$ alkyl group; the presence of this addition weak neutral donor site within the chelating cyclopentadienyl ligand framework may give rise to a tridentate ligand complex; more preferably, the donor group is —OMe, —OEt or —NMe$_2$. When such a donor group is present on R$^2$, it is not present on the cyclopentadienyl moiety, and viceversa.

In the titanium complexes of formula (I), p is preferably 2 and q is preferably 0; X is preferably Cl or Br. The substituents L are preferably the same and are preferably selected from the group consisting of C$_1$–C$_7$ alkyl groups, C$_6$–C$_{14}$ aryl groups and C$_7$–C$_{14}$ arylalkyl groups, optionally containing one or more Si or Ge atoms; even more preferably, the substituents L are selected from the group consisting of methyl, ethyl, n-butyl, sec-butyl, phenyl, benzyl and —CH$_2$Si(CH$_3$)$_3$. According to a favorite embodiment of the invention, L is methyl.

Preferred dihydrocarbyl titanium complexes produced with the process of the invention are the so-called constrained geometry catalysts; by the term "constrained geometry" as used herein is meant that the titanium atom in the metal coordination complex, and also in the catalyst resulting therefrom, is forced to greater exposure of the active catalyst site because of a specific ring structure of a ligand group including the Ti atom, wherein the metal is both bonded to an adjacent covalent moiety and held in association with the delocalized π-bonded cyclopentadienyl group through an η$^5$ or other π-bonding interaction. The concept of constrained geometry and specific constrain inducing ligand groups are described in EP-A-416,815; the complex must have a constrained geometry about the metal atom such that the angle at the metal between the centroid of the delocalized, substituted π-bonded moiety and the center of a constrain-inducing substituent is less than such angle in a comparative complex differing only in that said constrain-inducing substituent is replaced by hydrogen; more specifically, said angle is preferably less than 105°.

More preferably, in the present process is prepared a dihydrocarbyl titanium complex corresponding to formula (II):

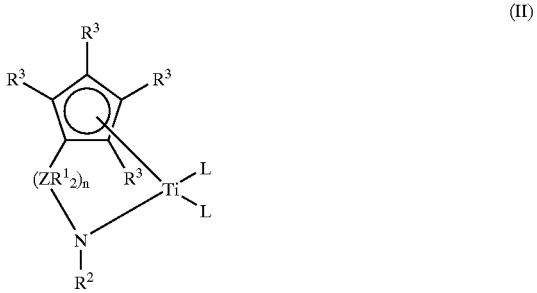

(II)

wherein:
R$^3$, the same or different from each other, are selected from the group consisting of hydrogen, linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl or C$_7$–C$_{20}$ arylalkyl groups, optionally containing Si, Ge, O, S, N or P atoms; or two or four adjacent R$^3$ groups form together one or more cycles;

the R$^2$ group on the amido moiety has the meaning reported above, and is most preferably selected from the group consisting of methyl, ethyl, propyl, butyl, pentyl, hexyl and isomers of these alkyl radicals, norbornyl, benzyl, phenyl, p-n-butyl-phenyl, cyclohexyl and cyclododecyl;

Z is C or Si; R$^1$ is defined as above and is most preferably selected from the group consisting of hydrogen, methyl, benzyl and phenyl; n is 1 or 2; L substituents have the meaning reported above and more preferably are methyl, neopentyl or benzyl.

Two or four adjacent R$^3$ groups on the cyclopentadienyl group may form one or two condensed rings; therefore, the Cp moiety is preferably selected from the group consisting of cyclopentadienyl, indenyl, tetrahydroindenyl, fluorenyl, tetrahydrofluorenyl and octahydrofluorenyl; R$^3$ groups on the foregoing cyclopentadienyl groups are independently selected from the group consisting of hydrogen, methyl, ethyl, butyl, pentyl, hexyl and isomers of these alkyl radicals, norbornyl, benzyl and phenyl.

A non limiting list of highly preferred compounds of formula (II) include:

ethylene(tert-butylamido)(tetramethyl-η$^5$-cyclopentadienyl)titanium dimethyl ethylene(tert-butylamido)(tetramethyl-η$^5$-cyclopentadienyl)titanium dibenzyl dimethylsilanediyl(tert-butylamido)(tetramethyl-η$^5$-cyclopentadienyl)titanium dimethyl dimethylsilanediyl(tert-butylamido)(tetramethyl-η$^5$-cyclopentadienyl)titanium dibenzyl dimethylsilanediyl(methylamido)(tetramethyl-η$^5$-cyclopentadienyl)titanium dimethyl dimethylsilanediyl(methylamido)(tetramethyl-η$^5$-cyclopentadienyl)titanium dibenzyl dimethylsilanediyl(phenylamido)(tetramethyl-η$^5$-cyclopentadienyl)titanium dimethyl dimethylsilanediyl(phenylamido)(tetramethyl-η$^5$-cyclopentadienyl)titanium dibenzyl dimethylsilanediyl(benzylamido)(tetramethyl-η$^5$-cyclopentadienyl)titanium dimethyl dimethylsilanediyl(benzylamido)(tetramethyl-η$^5$-cyclopentadienyl)titanium dibenzyl ethylene(tert-butylamido)(η$^5$-cyclopentadienyl)titanium dimethyl ethylene(tert-butylamido)(η$^5$-cyclopentadienyl)titanium dibenzyl dimethylsilanediyl(tert-butylamido)(η$^5$-cyclopentadienyl)titanium dimethyl dimethylsilanediyl(tert-butylamdido)(η$^5$-cyclopentadienyl)titanium dibenzyl dimethylsilanediyl(methylamido)(η$^5$-cyclopentadienyl)titanium dimethyl dimethylsilanediyl(methylamido)(η$^5$-cyclopentadienyl) dibenzyl dimethylsilanediyl(tert-butylamido)(indenyl)titanium dimethyl dimethylsilanediyl(tert-butylamido)(indenyl)titanium dibenzyl dimethylsilanediyl(benzylamido)(indenyl) titanium dimethyl and dimethylsilanediyl (benzylamido)(indenyl)titanium dibenzyl.

The process according to the present invention comprises the following steps, carried out in one reactor:

(1) reacting a ligand of formula (H—D)(ZR$^1{}_m$)$_n$(A—H) with about (2+p) molar equivalents of a compound of formula L$_j$B or LMgX, wherein D, A, Z, R$^1$, m, n, p, X and L have the meaning reported above; B is an alkaline or alkaline-earth metal; j is 1 or 2, j being equal to 1 when B is an alkaline metal, and j being equal to 2 when B is an alkaline-earth metal; and (2) reacting the product obtained from step (1) with about 1 molar equivalent of a compound of formula TiX$_4$, wherein X has the meaning reported above.

The hydrocarbyl titanium complexes of formulae (I) and (II) can be finally isolated from the reaction mixture obtained in step (2) and optionally purified according to standard procedures. Said process allows to obtain the hydrocarbyl titanium complexes of formulae (I) and (II) in very high yields, by means of a very practical and convenient one-pot reaction.

Surprisingly, it has been found that when reacting a suitable ligand with about 4 molar equivalents of a compound of formula $L_jB$ or LMgX and about 1 molar equivalent of a compound of formula $TiX_4$, the desired dihydrocarbyl titanium complexes are obtained, in high yield and high purity, with a one-pot reaction. Analogously, when reacting a suitable ligand with about 3 molar equivalents of a compound of formula $L_jB$ or LMgX and about 1 molar equivalent of a compound of formula $TiX_4$, the desired monohydrocarbyl titanium complexes are obtained, in high yield and high purity, with a one-pot reaction.

Moreover, it is not observed a significant reduction of Ti(IV) to Ti(III), that would lead to very poor reaction yields or would render necessary a further oxidation step; this is completely unexpected in the light of the processes reported in prior art literature, as already stressed above.

This new process typically provides the complexes of formulae (I) and (II) in yields of 60% and higher; the product complexes can be readily isolated in high purity by filtration, without the need of laborious purification procedures.

In the reactant $TiX_4$, the substituents X are preferably the same and are selected from the group consisting of —Cl, —Br, —OMe, —OEt, —OPr, —OBu and —OBz; said reactant is preferably selected from the group consisting of $TiCl_4$, $Ti(OEt)_4$, $Ti(OPr)_4$ and $Ti(OBz)_4$; it can be used even in the form of a stabilized derivative, such as an etherate complex of $TiX_4$.

$L_jB$ and LMgX are alkylating agents, wherein L is preferably a $C_1$–$C_8$ alkyl group, a $C_6$–$C_{14}$ aryl group or a $C_7$–$C_{14}$ alkylaryl group, optionally substituted with Si or Ge, and more preferably L is selected from the group consisting of methyl, ethyl, n-butyl, sec-butyl, phenyl, benzyl and —$CH_2Si(CH_3)_3$; even more preferably, L is methyl.

In the compound $L_jB$, B is an alkaline or alkaline-earth metal, and preferably Li or Mg; j can be 1 or 2, as already reported.

The compound LMgX is a Grignard reagent, wherein Mg is magnesium and L and X have the meaning reported above; X is preferably Cl or Br.

According to a preferred embodiment of the process of the invention, said alkylating agent is methyllithium.

The molar ratio of the compound of formula $L_jB$ or LMgX to the ligand of formula $(H-D)(ZR^1_m)_n(A-H)$ can vary within wide limits; an improved process for obtaining dihydrocarbyl complexes of formula (I), wherein p=2 and q=0, is obtained at ratios of about 4:1 and higher; an improved process for obtaining monohydrocarbyl complexes of formula (I), wherein p=1 and q=1, is obtained at ratios of about 3:1.

The molar ratio of the compound of formula $TiX_4$ to the ligand of formula $(H-D)(ZR^1_m)_n(A-H)$ is preferably about 1:1.

According to a preferred embodiment, the process of the invention is carried out in an aprotic solvent, either polar or apolar; said aprotic solvent is preferably an aromatic or aliphatic hydrocarbon or an ether, and more preferably it is selected from the group consisting of benzene, toluene, pentane, hexane, heptane, cyclohexane, diethylether, tetrahydrofurane and mixtures thereof.

According to another embodiment of the process of the invention, in step (1) said ligand $(H-D)(ZR^1_m)_n(A-H)$ is previously dissolved in an aprotic solvent and to the resulting solution is added the alkylating agent $L_jB$ or LMgX; this addition is preferably carried out at a temperature ranging from −80° C. to +50° C., and more preferably from −50° C. to +30° C. The alkylating agent is preferably added in the form of a solution in one of the above mentioned aprotic solvents. The thus obtained reaction mixture is preferably allowed to react, under stirring, at a temperature comprised between −80° C. and +50° C., more preferably between −50° C. and +30° C., and even more preferably at room temperature.

Before the reaction with $TiX_4$ in step (2), the mixture obtained from step (1) is preferably cooled to a temperature ranging from −80° C. to +50° C., and more preferably from −80° C. to room temperature; $TiX_4$ is then added to the cooled mixture, in the form of a solution in one of the above mentioned aprotic solvents, preferably pentane.

The reaction mixture is then allowed to react at a temperature comprised between −80° C. and +50° C., more preferably between −50° C. and +30° C., and even more preferably at room temperature.

The thus obtained titanium complexes of formula (I) and (II) can be isolated according to common procedures known in the state of the art.

The titanium complexes obtained with the process according to the present invention are useful in addition polymerization processes wherein, in association with an activating cocatalyst, they are contacted with one or more addition polymerizable monomers.

Addition polymerizable monomers include ethylenically unsaturated monomers, conjugated or non-conjugated dienes and polyenes. The hydrocarbyl titanium complexes are particularly useful in homo and co-polymerization of α-olefins of formula $CH_2=CHR$, wherein R is hydrogen or a $C_1$–$C_{20}$ alkyl, such as propylene, 1-butene, 1-pentene, 4-methyl-1-pentene, 1-hexene and 1-octene.

Other preferred addition polymerizable monomers include styrene, halo or alkyl substituted styrene, vinylbenzocyclobutane, 1,4-hexadiene, ethylidenenorbornene, cyclopentene and norbornene.

As reported above, the hydrocarbyl titanium complexes obtained with the process of the invention form suitable polymerization catalytic systems in association with activating cocatalysts, such as the ones described in EP-A-416,815. The term "activating cocatalyst" as used herein refers to a secondary component of the catalyst system able to cause the metal-containing complex to become effective as an addition polymerization catalyst or alternatively to balance the ionic charge of a catalytically activated species. Examples of the foregoing activating cocatalysts for use herein include alumoxanes, aluminum alkyls, aluminum halides, aluminum alkyhalides, Lewis acids, ammonium salts, non-interfering oxidizing agents and mixtures thereof.

Preferably the ratio of the hydrocarbyl titanium complex and cocatalyst on a molar basis is from about 1:0.1 to about 1:10,000, and more preferably from 1:1 to 1:1,000.

Suitable activating cocatalysts are linear alumoxanes having the following formula:

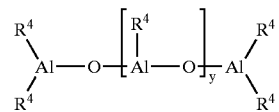

wherein $R^4$ is selected from the group consisting of halogen, linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing Si and Ge atoms, and y ranges from 0 to 40; $R^4$ is preferably methyl, ethyl, isobutyl or 2,4,4-trimethyl-pentyl; or cyclic alumoxanes having the following formula:

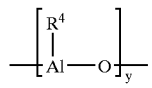

wherein $R^4$ has the meaning herein described and y is an integer ranging from 2 to 40.

Examples of alumoxanes suitable as activating cocatalysts in the catalysts according to the present invention are methylalumoxane (MAO), tetra-isobutyl-alumoxane (TIBAO), tetra-2,4,4-trimethylpentylalumoxane (TIOAO) and tetra-2-methyl-pentylalumoxane. Mixtures of different alumoxanes can also be used.

Suitable activating cocatalysts are also the products of the reaction between water and an organometallic aluminum compound, preferably of formula $AlR^4_3$ or $Al_2R^4_6$, wherein $R^4$ has the meaning reported above. Particularly suitable are the organometallic aluminum compounds of formula (II) described in EP-A-575,875, those of formula (II) described in WO 96/02580, those described in the WO 99/21899 and in the European app. no. 99203110.4. Non-limiting examples of organometallic aluminum compounds of formula $AlR^4_3$ or $Al_2R^4_6$ are: tris(methyl)aluminum, tris(isobutyl) aluminum, tris(isooctyl)aluminum, bis(isobutyl)aluminum hydride, methyl-bis(isobutyl)aluminum, dimethyl(isobutyl) aluminum, tris(isohexyl)aluminum, tris(benzyl)aluminum, tris(tolyl)aluminum, tris(2,4,4-trimethylpentyl)aluminum, bis(2,4,4-trimethylpentyl)aluminum hydride, isobutyl-bis(2-phenyl-propyl)aluminum, diisobutyl-(2-phenyl-propyl) aluminum, isobtityl-bis(2,4,4-trimethyl-pentyl)aluminum, diisobutyl-(2,4,4-trimethyl-pentyl)aluminum, tris(2,3-dimethyl-hexyl)aluminum, tris(2,3,3-trimethyl-butyl) aluminum, tris(2,3-dimethyl-butyl)aluminum, tris(2,3-dimethyl-pentyl)aluminum, tris(2-methyl-3-ethyl-pentyl) aluminum, tris(2-ethyl-3-methyl-butyl)aluminum, tris(2-ethyl-3-methyl-pentyl)aluminum, tris(2-isopropyl-3-methyl-butyl)aluminum and tris(2,4-dimethyl-heptyl) aluminum. Particularly preferred aluminum compounds are trimethylaluminum (TMA), tris(2,4,4-trimethylpentyl) aluminum (TIOA), triisobutylaluminum (TIBA), tris(2,3,3-trimethyl-butyl)aluminum and tris(2,3-dimethyl-butyl) aluminum.

Mixtures of different organometallic aluminum compounds can also be used. Further suitable activating cocatalysts are those compounds capable of forming an alkylmetallocene cation; preferably, said compounds have formula $Y^+Z^-$, wherein $Y^+$ is a Bronsted acid capable of donating a proton and of reacting irreversibly with a substituent X of the compound of formula (I), and $Z^-$ is a compatible non-coordinating anion, capable of stabilizing the active catalytic species which result from the reaction of the two compounds, and which is sufficiently labile to be displaceable by an olefinic substrate. Preferably, the $Z^-$ anion comprises one or more boron atoms. More preferably, the anion $Z^-$ is an anion of formula $BAr_4^{(-)}$, wherein the Ar substituents, the same or different from each other, are aryl radicals such as phenyl, pentafluorophenyl, bis (trifluoromethyl)phenyl. Tetrakis-pentafluorophenyl-borate is particularly preferred. Moreover, compounds of formula $BAr_3$ can be conveniently used.

The polymerization processes may be carried out in liquid phase, optionally in the presence of an inert hydrocarbon solvent either aromatic (e.g. toluene) or aliphatic (e.g. propane, hexane, heptane, isobutane, cyclohexane and 2,2,4-trimethylpentane), or in the gas phase.

The polymerization is conducted according to known techniques for Ziegler-Natta or Kaminsky-Sinn type polymerization, at a temperature generally ranging from about −30° C. to about 250° C., and preferably from 20 to 150° C., at reduced, elevated or atmospheric pressures. The molecular weight of the polymers can be varied by changing the type or the concentration of the catalytic components or by using molecular weight regulators, for example hydrogen. The catalyst may be used as it is or supported on a suitable organic or inorganic support, to provide a heterogeneous supported catalyst.

The following examples are given for illustrative and not limiting purposes.

GENERAL PROCEDURES AND CHARACTERIZATIONS

All operations were performed under nitrogen by using conventional Schlenk-line techniques. Solvents were purified by degassing with nitrogen and passing over activated alumina and subsequently stored under nitrogen.

BuLi (Aldrich), $Me_2SiCl_2$ (Aldrich), $NH_2^tBu$ (Aldrich), MeLi (Acros), piperidine (Aldrich), $TiCl_4$ and $ZrCl_4$ were used as received.

Indene (Aldrich) was purified by passing over activated alumina and subsequently stored under nitrogen.

All compounds were analyzed by $^1$H-NMR ($CDCl_3$, referenced against the peak of the residual $CHCl_3$ at 7.25 ppm) or $^{13}$C-NMR (Broad Band Decoupling, $CDCl_3$ referenced against the middle peak of $CDCl_3$ at 77.00 ppm), by using a AC200 Bruker spectrometer, operating at 200.13 MHz for $^1$H and 50.323 MHz for $^{13}$C. All NMR solvents were dried over $P_4O_{10}$ and distilled before use. Preparation of the samples was carried out under nitrogen, using standard inert atmosphere techniques.

GC-MS analysis were carried out on a HP5890 series 2 gas-chromatograph and a HP5970 mass spectrometer.

EXAMPLE 1

Synthesis of dimethylsilanediyl(tert-butylamido) (indenyl)titanium dimethyl (a) Synthesis of (indenyl)(dimethyl)chlorosilane $IndSiMe_2Cl$

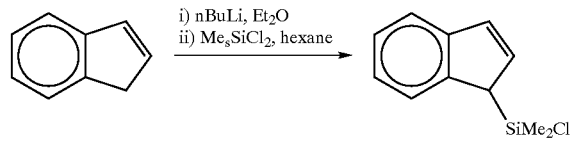

A solution of n-BuLi 2.5 M in hexane (37.5 ml, 93.75 mmoles) was added dropwise to a solution of indene (purity 90%, 11 ml, 84.9 mmoles) in 60 ml $Et_2O$, maintained under stirring at −78° C. (molar ratio indene:n-BuLi=1:1.1). At the end of the addition, the yellow slurry was allowed to reach room temperature and the reaction mixture was left under stirring for 4 hours to give an orange solution. The solvent was evaporated under reduced pressure to give a yellow solid, which was taken up in n-hexane (75 ml), thus obtaining a milky suspension, that was maintained under stirring for 5 minutes. Said suspension was filtered and the lithium salt of indene was separated as a white solid residue, which was washed with n-hexane (3×20 ml) in order to remove the unreacted indene.

The solid residue was re-suspended in n-hexane (40 ml) and added to a stirred solution of $Me_2SiCl_2$ (15.6 ml, 136.8 mmoles; $Me_2SiCl_2$/indLi=1.5) in hexane (50 ml), previously cooled to −78° C. At the end of the addition, the mixture was allowed to reach room temperature and was maintained under stirring overnight.

The suspension was then filtered, thus removing the solid residue LiCl, and the yellow solution obtained was brought to dryness in vacuo to yield a light yellow oil (16.5 g) of $IndSiMe_2Cl$, free from its vinylic isomer (yield 89%).

The product contained also a small quantity of the byproduct $Me_2SiInd_2$ (rac/meso=1:1.2; about 5%).

$^1$H-NMR ($CDCl_3$, 7.25 ppm): δ=0.21 (s, 3 H, Si—$CH_3$); 0.26 (s, 3H, Si—$CH_3$); 3.77 (br-t, J=1.87 Hz, 1H, Cp-H); 6.68 (dd, J=5.39, 1.87 Hz, 1H, Cp-H,); 7.03 (ddd, J=5.39, 1.87, 0.62 Hz, 1H, Cp-H); 7.19–7.36 (m, 2H, Ar), 7.48–7.52 (m, 1H, Ar), 7.57–7.61 (m, 1H, Ar).

GC-MS: [m/z]=208 [M$^+$], 115 [M$^+$-$SiMe_2Cl$], 93 [M$^+$-$C_9H_7$].

(b) Synthesis of (tert-butylamino)(dimethyl)(indenyl)silane $IndSiMe_2NHtBu$

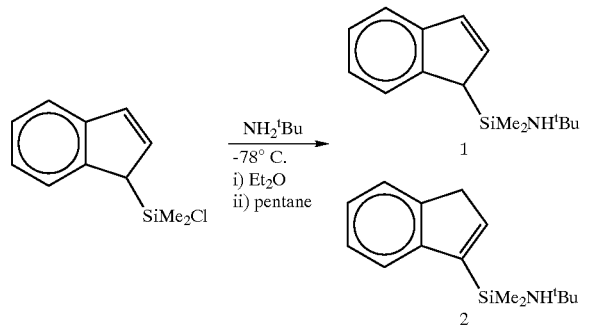

A solution of $IndSiMe_2Cl$ (5.6 g, 26.8 mmoles) in $Et_2O$ (10 ml) was added dropwise, under continuous stirring, to a solution of 6.6 ml of t-$BuNH_2$ (62.9 mmoles, t-$BuNH_2$;$IndSiMe_2Cl$=2.3) in $Et_2O$ (50 ml), cooled to −78° C. At the end of the addition, the mixture was allowed to reach room temperature and was left under stirring for 24 hours to give a white milky suspension. The solvent was evaporated under reduced pressure and the residue was extracted with n-pentane (40 ml). The suspension was filtered in order to remove the white ammonium salt t-$BuH_3NCl$ from the soluble product; the filtrate was concentrated in vacuo to give a light lemon yellow oil (5.46 g, 83%).

GC-MS, $^1$H-NMR and $^{13}$C-NMR analysis of the product showed the formation of $IndSiMe_2NH$-tBu as a mixture of two isomers (allyl isomer 1=75%; vinyl isomer 2=25%), with a total yield of 88%.

$^1$H-NMR ($CDCl_3$, 7.25 ppm): Isomer 1: δ=−0.01 (s, 3H, Si—$CH_3$); 0.03 (s, 3H, Si—$CH_3$); 0.72 (br-s, 1H, N—H); 1.28 (s, 9H, t-Bu); 3.68 (br-t, J=1.87 Hz 1H, Cp-H-1); 6.76 (dd, J=5.39, 1.87 Hz, 1H, Cp-H); 6.98 (ddd, J=5.39, 1.87, 0.62 Hz, 1 Cp-H); 7.15–7.40 (m, 2H, Ar), 7.5–7.61 (m, 2H, Ar).

$^1$H-NMR ($CDCl_3$, 7.25 ppm): Isomer 2: δ=0.44 (s, 6H, Si($CH_3$)$_2$); 0.9 (br-s, 1H, N—H); 1.22 (s, 9H, t-Bu); 3.47 (br-m, 2H, Cp-H-1); 6.87 (t, J=1.87 Hz, 1H, Cp-H-2); 3 aromatic protons overlap with those of the allylic isomer; 7.77 (d, 1H, Ar).

$^{13}$C-NMR ($CDCl_3$, 77 ppm): Isomer 1: δ=−0.60 (s, Si($CH_3$)$_2$); 0.16 (s, Si($CH_3$)$_2$); 34.28 (s, N—C($CH_3$)$_3$); 50.00 (s, C1); 50.08 (s, N—C($CH_3$)$_3$); 121.26–126.31 (C4–9); 129.12 (, C3); 135.46 (s, C2).

$^{13}$C-NMR ($CDCl_3$, 77 ppm): Isomer 2: δ=1.82 (s, Si($CH_3$)$_2$); 34.03 (s, N—C($CH_3$)$_3$); 41.02 (s, $CH_2$); 145.60 (s, C2).

GC-MS: [m/z]=245 [M$^+$], 130 [M$^+$-$C_9H_7$], 115 [M$^+$-$SiMe_2NH^tBu$].

(c) Synthesis of dimethylsilanediyl(tert-butylamido)(indenyl)titanium dimethyl [$IndSiMe_2N^tBu$]$TiMe_2$

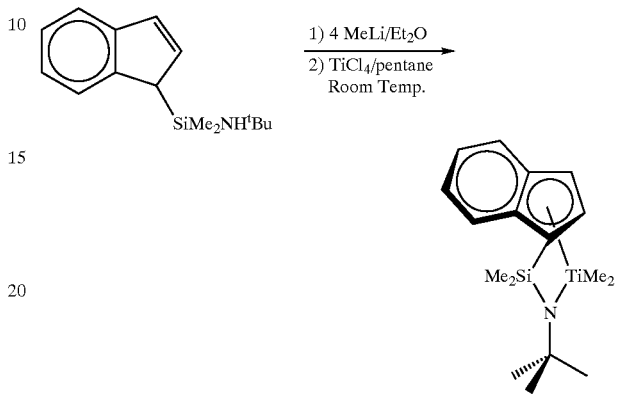

11.30 ml of a solution of MeLi 1.6 M in $Et_2O$ (18.04 mmoles) were slowly added at −78° C. to a solution containing 1.08g (4.40 mmoles) of (tert-butylamino)(dimethyl)(indenyl)silane $IndSiMe_2NH^tBu$ in 23 ml of $Et_2O$ (the molar ratio $IndSiMe_2NH^tBu$/MeLi=1:4.2). During the addition an increasing turbidity developed with final formation of a yellow suspension. The mixture was stirred for 2 hours at room temperature.

To the suspension was slowly and cautiously added, at room temperature, a mixture of 0.5 ml of $TiCl_4$ (4.40 mmoles) in 23 ml n-pentane (the molar ratio $IndSiMe_2NHtBu$/$TiCl_4$=1:1). The mixture turned quickly to dark green color with a consistent development of gas; at the end of the addition a brown suspension was obtained. Such suspension was stirred overnight. The reaction mixture was then brought to dryness under reduced pressure. The dark solid was extracted with 60 ml of toluene and then the filtrate was evaporated to dryness under reduced pressure to give 0.99 g (70% yield) of a gray-black solid. Its $^1$H-NMR analysis confirmed the formation of [$IndSiMe_2N^tBu$]$TiMe_2$.

$^1$H-NMR ($CDCl_3$, 7.25 ppm): δ=−0.553 (s, 3H, Ti($CH_3$)$_2$); 0.479 (s, 3H, Si($CH_3$)$_2$) 0.535 (s, 3H, Si($CH_3$)$_2$); 0.706 (s, 3H, Ti($CH_3$)$_2$); 6.220 (d, 1H, H2, $^3j_{HH}$=3 Hz); 7.048–7.129 (m, 1H, arom); 7.263–7.344 (m, 2H, arom and H3); 7.457–7.504 (m, 1H, arom); 7.744–7.791 (m, 1H, arom).

$^1$H-NMR ($C_6D_6$, 7.16 ppm): δ=−0.15 (q, J=0.48 Hz, 3H, Ti—$CH_3$); 0.36 (s, 3H, Si—$CH_3$); 0.53 (s, 3H, Si—$CH_3$); 0.82 (q, j 0 0.48 Hz, 3H, Ti—$CH_3$); 1.44 (s, 9H, t-Bu); 6.05 (d, J=3.21, 1H, Cp-H2); 6.88 (ddd, J=8.50, 6.64, 1.04 Hz, 1H, Ar—H6); 7.01 (dd, J=3.21, 0.83 Hz, 1H Cp-H3); 7.07 (ddd, J=8.50, 6.64, 1.04 Hz, 1H, Ar—H5); 7.46 (dq, J=8.50, 1.04 Hz, 1H, Ar—H7); 7.48 (dt, J=8.50, 1.04 Hz, 1H, Ar—H4).

The reaction yield of dimethylsilanediyl(tert-butylamido)(indenyl) titanium dimethyl, obtained with the one-step process according to the present invention (70%), is much higher than the one obtainable with the two reaction steps according to the literature procedures (lower than 42%), as already reported in the prior art description.

EXAMPLE 2

Synthesis of dimethylsilanediyl(tert-butylamido)(tetramethyl-$\eta^5$-cyclopentadienyl)titanium dimethyl

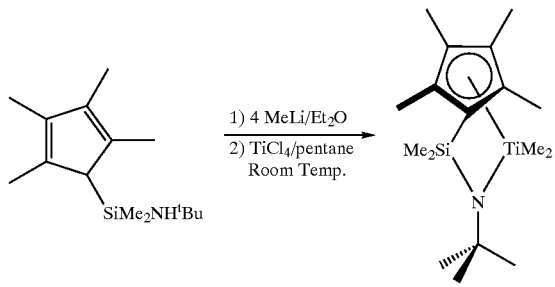

20.9 ml of a solution of MeLi 1.6 M in Et$_2$O (33.52 mmoles) were slowly added at −78° C. to a solution containing 2.0 g (7.98 mmoles) of (tert-butylamino)(dimethyl)(tetramethyl-cyclopentadi-2,4-enyl)silane Me$_4$CpSiMe$_2$NHt-Bu in 43 ml of Et$_2$O (the molar ratio Me$_4$CpSiMe$_2$NHtBu/MeLi=1:4.2). During the addition, an increasing turbidity developed, with final formation of a white dense suspension. The mixture was allowed to warm to room temperature and then stirred for 2 hours.

To said suspension was added, at room temperature, a mixture of 0.88 ml of TiCl$_4$ (7.98 mmoles) in 43 ml n-pentane (the molar ratio Me$_4$CpSiMe$_2$NHt-Bu/TiCl$_4$=1:1). The mixture turned quickly to a dark green color with a consistent development of gas; at the end of the addition a black suspension was obtained, which was stirred at room temperature overnight. The reaction mixture was then brought to dryness under reduced pressure. The dark solid was extracted with 120 ml of toluene and then the filtrate was evaporated to dryness under reduced pressure to give 1.51 g (60% yield) of a black solid. $^1$H-NMR showed the presence of chemically pure dimethylsilanediyl(tert-butylamido)(tetramethyl-$\eta^5$-cyclopentadienyl) titanium dimethyl.

$^1$H NMR (δ, ppm, C$_6$D$_6$; ref. C$_6$D$_5$H at 7.16 ppm): 0.43 (s, 6H, Si—CH$_3$), 0.49 (s, 6H, Ti—CH$_3$), 1.56 (s, 9H, t-Bu), 1.85 (s, 6H, Cp-CH3), 1.96 (s, 6H, Cp-CH3).

The reaction yield of dimethylsilanediyl(tert-butylamido)(tetramethyl-$\eta^5$-cyclopentadienyl) titanium dimethyl, obtained with the one-step process according to the present invention (60%), is much higher than the one obtainable with the two reaction steps according to the literature procedures (lower than 32%), as already reported in the prior art description.

What is claimed is:

1. A process for the preparation of titanium complexes of formula (I):

$$(D)(ZR^1{}_m)_n(A)TiL_pX_q \quad (I)$$

wherein:

$(ZR^1{}_m)_n$ is a divalent group bridging D and A; Z is selected from the group consisting of C, Si, Ge, N, P and B; the $R^1$ groups, the same or different from each other, are selected from the group consisting of hydrogen, linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl and C$_7$–C$_{20}$ arylalkyl groups, or two $R^1$ groups form together a cycle; m is 1 or 2; n is an integer ranging from 1 to 3;

D is a delocalized π-bonded moiety, which is bound in a $\eta^5$ bonding mode to Ti;

A is a divalent anionic group selected from —O—, —S—, —N(R$^2$)— and —P(R$^2$)—, wherein R$^2$ is hydrogen, a linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl or C$_7$–C$_{20}$ arylalkyl, optionally containing —OR', —SR', —NR'$_2$ or —PR'$_2$ groups, wherein R' is a C$_1$–C$_{10}$ alkyl group;

Ti is titanium;

the substituents L, same or different from each other, are monoanionic sigma ligands selected from the group consisting of linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl and C$_7$–C$_{20}$ arylalkyl groups, optionally containing one or more Si or Ge atoms;

X is halogen or —OR', wherein R' is a C$_1$–C$_{10}$ alkyl group;

p is 1 or 2; q is 0 or 1, and p+q=2;

said process being characterized by comprising the following steps:

(1) reacting a ligand of formula (H—D)(ZR$^1{}_m$)$_n$(A—H) with about (2+p) molar equivalents of a compound of formula L$_j$B or LMgX, wherein D, A, Z, R$^1$, m, n, p, X and L have the meaning reported above; B is an alkaline or alkaline-earth metal; j is 1 or 2, j being equal to 1 when B is an alkaline metal, and j being equal to 2 when B is an alkaline-earth metal; and (2) reacting the product obtained from step (1) with about 1 molar equivalent of a compound of formula TiX$_4$, wherein X has the meaning reported above.

2. The process according to claim 1, wherein $(ZR^1{}_m)_n$ is selected from the group consisting of CR$^1{}_2$, (CR$^1{}_2$)$_2$, (CR$^1{}_2$)$_3$, CR$^1$=CR$^1$, SiR$^1{}_2$, (SiR$^1{}_2$)$_2$, CR$_2$—SiR$_2$, GeR$^1{}_2$, NR$^1$, PR$^1$ and BR$^1$, R$^1$ having the meaning reported in claim 1.

3. The process according to claim 2, wherein $(ZR^1{}_m)_n$ is selected from the group consisting of Si(CH$_3$)$_2$, SiPh$_2$, CH$_2$, (CH$_2$)$_2$, (CH$_2$)$_3$ and C(CH$_3$)$_2$.

4. The process according to claim 1, wherein D is a substituted or unsubstituted cyclopentadienyl group, optionally condensed to one or more substituted or unsubstituted, saturated, unsaturated or aromatic rings.

5. The process according to claim 4, wherein D is selected from the group consisting of cyclopentadienyl, mono-, di-, tri- and tetra-methyl cyclopentadienyl; 3-tbutyl-cyclopentadienyl; 3-adamantyl-cyclopentadienyl; indenyl; 2-methyl-indenyl; 4,7-dimethyl-indenyl; 3-tbutyl-indenyl; 3-isopropyl-indenyl; benzoindenyl; 4,5,6,7-tetrahydroindenyl; fluorenyl; tetrahydrofluorenyl; octahydrofluorenyl; N-methyl- and N-phenyl-5,10-dihydroindeno [1,2-b]indol-10-yl; N-methyl- and N-phenyl-5,6-dihydroindeno[2,1-b]indol-6-yl; azapentalene-4-yl; thiapentalen-4-yl; azapentalen-6-yl; thiapentalen-6-yl; mono-, di- and tri-methyl-azapentalen-4-yl.

6. The process according to claim 1, wherein said divalent anionic group A is —N(R$^2$)— or —P(R$^2$) and —R$^2$ is selected from the group consisting of methyl, ethyl, propyl, butyl, pentyl, hexyl and isomers of these alkyl radicals, norbornyl, benzyl and phenyl.

7. The process according to claim 1, wherein p is 2, q is 0 and the substituents L are the same and are selected from the group consisting of methyl, ethyl, n-butyl, sec-butyl, phenyl, benzyl and —CH$_2$Si(CH$_3$)$_3$.

8. The process according to claim 1, wherein said titanium complex corresponds to formula (II):

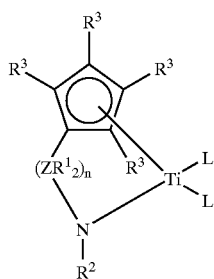

wherein:

R$^1$, R$^2$ and L have the meaning reported in claim 1; Z is C or Si; n is 1 or 2;

R$^3$, the same or different from each other, are selected from the group consisting of hydrogen, linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl or C$_7$–C$_{20}$ arylalkyl groups, optionally containing Si, Ge, O, S, N or P atoms, or two or four adjacent R$^3$ groups form together one or more cycles.

9. The process according to claim 8, wherein R$^1$ is selected from the group consisting of hydrogen, methyl, benzyl and phenyl; R$^2$ is selected from the group consisting of methyl, ethyl, propyl, butyl, pentyl, hexyl and isomers of these alkyl radicals, norbomyl, benzyl, phenyl, p-n-butyl-phenyl, cyclohexyl and cyclododecyl; R$^3$ is selected from the group consisting of hydrogen, methyl, ethyl, butyl, pentyl, hexyl and isomers of these alkyl radicals, norbomyl, benzyl and phenyl, or two or four adjacent R$^3$ groups form one or two condensed rings; the substituents L are the same and are selected from the group consisting of methyl, neopentyl and benzyl.

10. The process according to claim 1, wherein in the reactant TiX$_4$, the substituents X are the same and are selected from the group consisting of —Cl, —Br, —OMe, —OEt, —OPr, —OBu and —OBz.

11. The process according to claim 1 wherein, in the compounds of formulae L$_j$B and LMgX, L is selected from the group consisting of methyl, ethyl, n-butyl, sec-butyl, phenyl, benzyl and —CH$_2$Si(CH$_3$)$_3$; j is 1 or 2; B is Li or Mg; and X is Cl or Br.

12. The process according to claim 11, wherein L is methyl.

13. The process according to claim 1, characterized by being carried out in an aprotic solvent.

14. The process according to claim 1, wherein in step (1), said ligand (H—D)(ZR$^1_m$)$_n$(A—H) is first dissolved in an aprotic solvent and to the resulting solution is added L$_j$B or LMgX, and finally TiX$_4$ is added.

15. The process according to claim 14, wherein said aprotic solvent is selected from the group consisting of benzene, toluene, pentane, hexane, heptane, cyclohexane, diethylether, tetrahydrofurane and mixtures thereof.

* * * * *

UNITED STATES PATENT AND TRADEMARK OFFICE
CERTIFICATE OF CORRECTION

PATENT NO. : 6,774,253 B1
DATED : August 10, 2004
INVENTOR(S) : Luigi Resconi

Page 1 of 1

It is certified that error appears in the above-identified patent and that said Letters Patent is hereby corrected as shown below:

Column 16,
Line 36, change "$CR_2\text{-}SiR_2$" to -- $CR^1_2\text{-}SiR^1_2$ --

Signed and Sealed this

Twenty-eighth Day of December, 2004

JON W. DUDAS
*Director of the United States Patent and Trademark Office*